United States Patent [19]
Roth et al.

[11] Patent Number: 4,523,590
[45] Date of Patent: Jun. 18, 1985

[54] METHOD AND DEVICE FOR REVERSIBLE STERILIZATION IN MAMMALS

[76] Inventors: Wilfred Roth, 185 S. Cove Rd., Burlington, Vt. 05401; C. Irving Meeker, 196 Winn Rd., Falmouth, Me. 04105

[21] Appl. No.: 436,292

[22] Filed: Oct. 25, 1982

[51] Int. Cl.³ .............................................. A61B 17/12
[52] U.S. Cl. .................... 128/325; 128/1 R
[58] Field of Search .................... 128/1 R, 303 R, 325, 128/346, 126–130

[56] References Cited

U.S. PATENT DOCUMENTS

| 3,056,408 | 10/1962 | Brown | 128/325 |
| 3,326,217 | 6/1967 | Kerr | 128/325 |
| 3,648,683 | 3/1972 | Brodie | 128/1 R |
| 4,416,266 | 11/1983 | Baucom | 128/325 |

FOREIGN PATENT DOCUMENTS 1530282 10/1978 United Kingdom ............... 128/1 R
2010728 7/1979 United Kingdom ............... 128/1 R

OTHER PUBLICATIONS

Sciarra, J. J., Zatuchni, G. I., Speidel, J. J. (eds), *Reversal of Sterilization*, Harper & Row, pp. 226–231 (1977).
Sciarra, J. J., Droegemueller, W., Speidel, J. J. (eds), *Advances in Female Sterilization Techniques*, Harper & Row, pp. 91–99 (1975).

*Primary Examiner*—Edward M. Coven
*Attorney, Agent, or Firm*—Pennie & Edmonds

[57] ABSTRACT

This invention relates to a method and device for effecting reversible sterilization in mammals. Specifically, the invention discloses means for occluding the fallopian tubes through the combined use of a notched plug inserted into each fallopian tube and a clip applied externally around a portion of the tube containing the plug.

13 Claims, 5 Drawing Figures

METHOD AND DEVICE FOR REVERSIBLE STERILIZATION IN MAMMALS

TECHNICAL FIELD

This invention relates to a device for use in effecting reversible sterilization in mammals. More particularly, it discloses the combined use of a notched plug inserted into and a specially configured clip placed around the fallopian tube. This invention also relates to a method for reversible sterilization using the disclosed combination of the external clip and internal plug.

BACKGROUND ART

Various procedures have been proposed for effecting reversible sterilization in the human female. Ideally, the method of choice should be a safe and effective means of contraception for the desired sterilization period which provides an acceptable probability of successful reversibility. Tubal sterilization methods characterized by varying degrees of reversibility include: tubal ligation procedures, as well as tubal occlusion by means of fulguration, application of clips, bands or rings, chemically-induced occlusion or implantation of intratubal plugs. Factors to be considered with any type of tubal sterilization method include the effect of the procedure on tubal tissue, as well as, potential tissue reaction, tube distortion, tissue sensitivity, risk of infection, damage during installation and removal of the sterilization device and necessity for surgical reanastomosis to restore tubal patency.

One known method of tubal occlusion involves the application of external clips to the fallopian tubes. A major drawback of the use of such clips is that the portion of the tube which is under direct pressure of the clip becomes crushed. Reversal of this sterilization method thus requires surgical excision of the necrosed section and reanastomosis of the remaining intact portions of the tube. When the clip pressure is high, the possibility of irreversible tissue damage becomes a concern due to continued interruption of blood supply to the involved tissue. The external clips may also expand with time, exert insufficient pressure due to tissue shrinkage, or become dislodged, thus allowing the tube to reopen. If the clips are made of metal materials, the possibility of tissue reaction must also be considered.

In an attempt to avoid various problems inherent in the method of clip compression of the fallopian tubes, the use if intratubal plugs has been proposed. A major consideration prompted by this tubal occulsion method is that the plug material be nontoxic and non-irritating to the surrounding tissue. The use of a plug alone, however, is not fully effective in all cases due to various factors such as tissue wall thickness shrinkage with time, ultimately leading to axial slippage of the plug.

The problem of maintaining complete tubal occlusion has been approached through the use of suture material tied around that portion of the tube containing an internal plug. The goal of this method is to effect compression of the single layer of tubal tissue located between the suture and the plug, "A Tubal Occlusive Device in Monkeys", In Sciarra, J. J., Zatuchni, G. I., Spiedel, J. J. (eds) *Reversal of Sterilization,* Harper & Row, pp. 226 (1977). With the use of sutures, comes the problem of tissue reaction to a given suture material. The suture/plug combination also poses installation as well as removal problems. For example, the suture material, over time, may become buried in the wall of the tube and subsequent plug removal necessitates cutting of the tissue. The fibrin which overgrows any foreign material in the peritoneal cavity can ultimately bury the suture material. Removal of the suture material most often causes significant damage of the tube tissue. Tearing or major disruption of the plug site has also been observed in some cases. In many instances, the suture material can cut through the tube during the removal process.

Steptoe has proposed the use of a solid silastic intratubal device having a nylon thread core, "The Potential Use of Intratubal Stents for Reversible Sterilization", In Sciarra, J. J., Droegemueller, W., Spridel, J. J. (eds) *Advances in Female Sterilization Techniques,* Harper & Row, pp. 91 (1976). The intratubal stent averages a length of 4 cm or 6 cm. and has protuberances at fixed intervals. Between a given pair of protuberances, an external tantalum locking clip is applied. Drawbacks of the device are that a high degree of technical skill is required for insertion of the device and specially designed instruments must be used for implantation.

SUMMARY OF THE INVENTION

The present invention relates to a device and method for achieving reversible sterilization in mammals and, in particular, humans by means of fallopian tube occlusion. The need for external sutures to effect positive closure between an internally-located plug and the inner wall of the fallopian tube is eliminated by the use of a specially designed external clip which surrounds the portion of the tube containing the internal plug, Meeker, C. I., Roth, W., "A Method For Reversible Sterilization In The Female", Paper Delivered at the 19th Annual Meeting of the Association of Planned Parenthood Physicians (Oct. 29–31, 1981), hereby incorporated by reference. Fallopian tube tissue necrosis, adhesion or disruption, which are potential results of the use of external sutures, are avoided by the use of the external clip according to the invention. Advantageously, the device is readily installed and removed without the need for cutting tubal tissue. The concept of an internal blocking means, such as a plug, used in combination with sn external retaining means, such as a clip, according to this invention can advantageously be applied in any situation in which the desired effect is occlusion of a flexible-wall tube-like structure and solid internal blocking means.

Broadly, the device according to the invention comprises blocking means, such as a plug, adapted for insertion into the fallopian tube at a predetermined location and means configured and dimensioned to be positioned about the portion of the fallopian tube containing the blocking means to resiliently retain the blocking means at the predetermined location. The retaining means, for example, a flexible clip, defines at least one aperture for reception of a portion of the fallopian tube and means for selectively varying the dimension of the aperture to facilitate selective positioning about the fallopian tube as well as removal therefrom.

DESCRIPTION OF THE PREFERRED EMBODIMENTS

Figure 1:
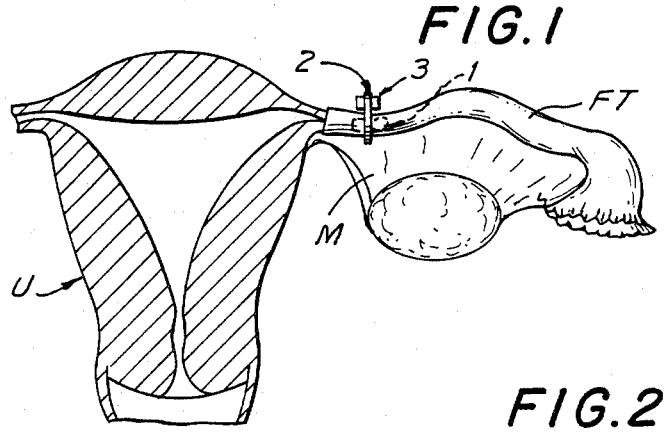
FIG. 1 is a schematic view of the device according to the invention in place within the body.

FIG. 1 represents a schematic view of the device according to the invention in place within the human body. A solid plug 1 has been inserted via the fimbriated end of the fallopian tube FT to a predetermined location. A portion of the tube containing the plug is surrounded by an external clip 2 into which a locking barrel 3 has been inserted.

Figure 2:
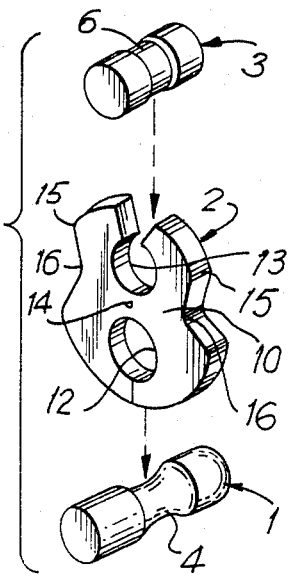
FIG. 2 is an exploded perspective of the individual components of the device according to the invention.

FIG. 2 represents an exploded perspective of the individual components of the device which broadly comprises a solid plug 1, an external clip 2 and a locking barrel 3.

Figure 3:
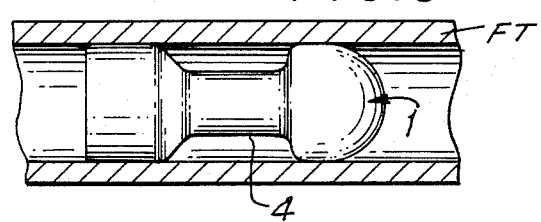
FIG. 3 is a schematic view of the plug component of the device in place within the fallopian tube according to the invention.

FIG. 3 represents a schematic view of the solid plug component 1 of the device in place within the fallopian tube FT. The plug comprises a biologically compatible material which can be plastic such as, for example, polytetrafluoroethylene or Teflon, and is grooved in shape so that it is characterized by at least a single notch or groove 4. The dimensions of the plug are between about 5.0 mm and 7.0 mm in length and between about 1.0 mm and 4.0 mm in outside diameter at the end portions. The notched portion 4 of the plug measures about 2.0 mm in length. The diameter of the notch is between about 0.3 mm and 2.8 mm. The depth of the notch—the difference between the inside core and the outside diameter—is such that the clearance in relation to the surrounding tube wall ranges between about 0.35 mm and 0.6 mm. The total clearance between the clip and the center of the plug is between about 0.7 mm and 1.2 mm. The depth of the notch is such that tubes of varying thickness may be accommodated, permitting occlusion without destruction of any intervening tissue.

Figure 4:
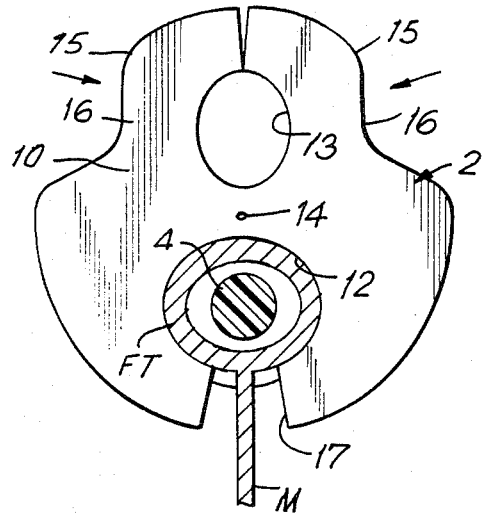
FIG. 4 is a schematic view of the external clip opened to surround a portion of the fallopian tube containing the plug according to the invention.
Figure 5:
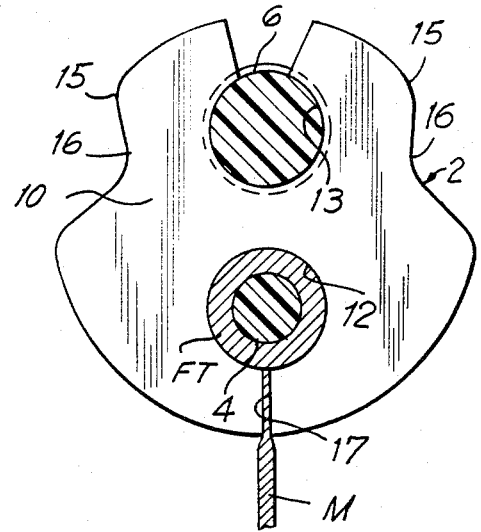
FIG. 5 is a schematic view of the external clip closed to surround a portion of the fallopian tube containing the plug according to the invention.

FIGS. 4 and 5 represent schematic views of an external flexible clip 2 for use in combination with the internal plug according to the invention. The function of the clip is to surround that portion of the fallopian tube containing the plug and, specifically, the notched area of the plug, to provide a sufficiently tight seal between the inner walls of the tube and the plug and insure complete occlusion of the tube so that ova and sperm are effectively prevented from flowing around the plug.

The clip 2 is made of biologically compatible material which can be plastic such as, for example, polytetrafluoroethylene or Teflon, and is characterized by a body portion 10 defining two apertures 12, 13 located on either side of a flexible web 14 between them that functions as a flexible hinge. Alternatively, the clip may be made of any metal which would be biologically compatible, anti-inflammatory and non-erodible. The clip 2 has opposed members 15 and indentations 16 on either side and a slit portion 17 such that when pressure is applied to the indentations, the flexible hinge acts to open the slit and the first aperture 12. Slit portion 17 is advantageously designed so that the clip does not perforate the mesosalpinx M. Although the mesosalpinx M is compressed, the small blood vessels contained within remain intact and blood supply to the fallopian tube FT is maintained. The second aperture 13 is adapted to accept a locking barrel 3 which functions to facilitate closure pressure to the tube exerted by the walls of the second aperture 13. When inserted into aperture 13, the locking barrel insures that the clip will not open to restore tubal patency.

Aperture 12 is designed for reception of a portion of the fallopian tube FT. Aperture 13 is defined in part by the opposed members 15 which are adapted to be moved toward and away from each other. The opposed members 15 are connected to the portion of the body member defining aperture 12, for movement toward and away from each other to vary the dimension of aperture 12.

The clip 2 is designed and adapted to retain a given dimensioned plug 1 within the fallopian tube FT at a preselected location. It locks into position around the area of the tube surrounding the notched portion 4 of the plug 1, to prevent axial slippage of the plug as well as flow of ova and sperm around it. The size of the particular clip used will depend upon the dimensions of the plug to be inserted into the tube. The clip itself has a thickness of about 1.0 mm. The outside diameter of the clip is about 7.0 mm. At one end of the clip, aperture 13, which has a diameter of about 1.8 mm, functions to accept the cylindrical locking barrel 3, which is about 3.0 mm in length and has a diameter, at its ends, of about 2.0 mm. The locking barrel itself has a notched portion 6 of about 1.8 mm in diameter and about 1.2 mm in length.

The first aperture in the clip, aperture 12, has a diameter equal in size to the outside diameter of the plug, i.e. between about 1.0 mm and 4.0 mm. This assures adequate clearance for thicker tubes, which require plugs having deeper notches, as well as for thinner tubes, which require plugs having shallower notches. When the clip 2 is applied to the fallopian tube FT, aperture 12 surrounds that portion of the tube located adjacent to the notched area of the plug. At the end of the clip nearest to aperture 13, two indentations 16 in the wall of the clip are present. The indentations serve as points onto which forceps can attach in order to open the clip 2 by the action of the flexible hinge 14, located in the central portion of the clip. The slit portion 17 located at the end of the clip opposite to aperture 13, opens to allow aperture 12 to surround the tube at a point opposite to the notch 4 in the plug.

The device of the invention is installed as follows. The notched plug 1 is inserted to the desired position in the fallopian tube FT via the fimbriated end of the tube during the course of a minilaparotomy procedure. In the minilaparotomy procedure, a small incision of about 4 cm in length is made transversely at, or just above, the pubic hairline. The incision is carried down to the fascia which, itself, is incised. The rectus muscles are retracted laterally and the peritoneal cavity is entered. A narrow retractor is inserted to expose the adnexa on one side. The fallopian tube FT and round ligament are identified at their insertion into the uterus U. The tube is then followed laterally using an atraumatic Babcock clamp moved distally along the tube until the fimbriated end of the tube is identified.

The fimbriated end is then brought into view in the incision. The mesosalpinx M is then manually grasped around the tube so that the plug 1 can be inserted through the fimbriated end of the tube to approximately the midpoint of the tube using introducing or inserting means. The plug is then grasped through the tube to stabilize it while the introducing or inserting means is removed from inside the tube.

By means of a clip applicator, the clip 2 is delivered through the incision to the external area of the fallopian tube FT surrounding the internal plug 1. The clip applicating means may be, for example, a modified hemostat or modified forceps. Under one embodiment, a standard thumb forcep has been modified by squaring the end, cutting a small v-shaped notch in each side and then bending the tip of the forceps, including the notch, at 90 degrees so that the four resulting points are facing each other. Such a notched forceps is advantageously used to pick up the clip and, by closing the forceps, to close the aperture 13 that will surround the locking barrel 3, thus opening the aperture 12 that will surround the plug and tube. The clip is opened by placing the ends of a modified forceps into each of the indentations 16 in the clip. As the indentations are squeezed, the flexible hinge 14 allows the slit portion 17 and aperture 12 to open. Aperture 12, in the opened position, is slipped around the fallopian tube FT and positioned at the notched portion of the plug. The forceps are removed and the clip 2 is manually squeezed so that the slit portion 17 closes around the fallopian tube to compress but not perforate the mesosalpinx M. A modified forceps or a modified hemostat is inserted into small identations located on either side of the locking barrel 3, which is inserted into aperture 13 of the clip. These forceps, for example, have been modified so that the tip remains somewhat sharp and bent at right angles towards its opposite side. Alternatively, a small towel clip may be used to hold the plug securely. The locking barrel snaps into place in aperture 13 and functions to apply closure pressure to the fallopian tube by means of the walls of aperture 12.

The fallopian tube containing the plug and clip is returned to the peritoneal cavity. Subsequently, the retractor is moved to the opposite end of the incision and the second fallopian tube is similarly identified and grasped. The plug insertion and clip securing procedure are repeated as described above for the first fallopian tube. The incision is then closed in layers.

In order to remove the clip 2 and plug 1, the reverse process is followed. Any fibrin which has coated the clip is dissected from the clip so that the tubal wall remains intact although compressed. The locking barrel 3 is removed from aperture 13 using modified forceps. The clip is manually squeezed so that the slit portion 17 opens. Modified forceps are placed into each of the indentations 16 of the clip and the clip is squeezed, causing the flexible hinge 14 to allow both aperture 13 and the slit portion to open completely. The clip 2 is then slipped off of the fallopian tube FT. The plug 1 is removed by a "milking" action by which the tube is taken hold of and pressure applied so that the plug is progressively squeezed along the length of the tube. Alternatively, the plug may be removed through a slit made in the tube at the point of the plug. The plug is then pushed out of the tube through the slit.

Advantageously, the apertures 12,13 need not have the same diameter. Under one embodiment of the invention, the locking barrel 3 and aperture 13 have the same diameter as internal plug 1 and aperture 12. In addition, for the occlusion of tubes characterized by a high degree of wall and mesosalpinx thickness, the slit portion 17 can be made in such a way that a gap is present when it is closed.

As an alternative to the minilaparotomy procedure for insertion of the plug and clip, delivery of these sevices may be effected by a colpotomy approach.

REVERSIBLE TUBAL OCCLUSION USING THE PLUG AND CLIP COMBINATION

Tubal occlusion by means of the combined use of an internal plug and an external clip according to the invention was studied using the baboon as an animal model. Plugs and clips of two different sizes were prepared and randomly implanted into seven baboons. The devices were left in place for a period of six months, during which the animals were bred regularly without resulting conception.

In the four animals implanted with small clips, insufficient clearance was maintained between the clips and the plugs and the tubes were severed at that point. In the three animals implanted with the larger clips, the clearance between the clips and the plugs were adequate and the clips were easily dissected free of fibrin sheath covering for removal. After removal of the clips and plugs from these animals, the fallopian tubes were both patent and intact, as demonstrated by the injection of methylene blue dye. Two months later, salpingectomies were performed and the plug site was examined by scanning electron microscopy. Examination indicated no major disruption of the tubal structure.

Modified clips and plugs were designed to assure adequate clearance between them when implanted. The devices were implanted into twenty adult female baboons. During a five month period, the animals were bred with plug and clip devices in place 95 times—or 4.8 times per animal—with no resulting pregnancies. The devices were removed from two of the animals. The clips had become covered with fibrin and single small adhesions from the clips to the adjacent omentum were present in some instances. The devices were removed without difficulty after the adhesions were ligated and the fibrin sheaths were dissected free. The tubes were distended with saline and tubal patency was indicated by the absence of any leakage.

Breeding of all of the animals was continued and the clip and plug devices were removed from fifteen additional animals at a period in time twelve months after implantation. After removal of the devices, the degree of reversibility was determined by breeding until pregnancy occurred, or for twelve months following removal. All animals were bred at least three times after removal of the plugs. A total of seven animals become pregnant or successfully delivered. This represents 43.8% of the sixteen animals that could conceive at the time. The animals that conceived did so on their first, second, third, fourth, fifth or sixth breeding cycle after plug removal. The remaining nine animals with the devices removed were bred a total of 44 times—or an average of 4.9 times per animal. Two of the animals died during the course of observation due to problems unrelated to the experiment. One of these belonged to the group of fifteen from which the devices were removed and the other was one of the three in which the devices were still implanted. Devices were removed from the remaining two animals eighteen months after implantation.

Having described the invention with particular reference to the preferred form thereof, it will be obvious to those skilled in the art to which the invention pertains, after understanding the invention, that various changes and modifications may be made therein without departing from the spirit and scope of the invention as defined by the claims appended hereto.

We claim:

1. A device for effecting reversible sterilization in female mammals by means of occlusion of the fallopian tubes which comprises:
   (a) blocking means for insertion into a fallopian tube, said blocking means comprising at least one notched or grooved portion between two end portions, said at least one notched or grooved portion being smaller in diameter than the diameter of said end portions, which end portions, in turn, are smaller in diameter than the inside diameter of said fallopian tube;
   (b) flexible retaining means comprising a body portion having at least two apertures, at least one slit portion, and opening means for opening one of said at least two apertures and said slit portion for reception of the mesosalpinx and the portion of said fallopian tube which surrounds said blocking means; and
   (c) locking means configured and dimensioned to fit into a second aperture of said flexible retaining means and apply force to close said first aperture of said flexible retaining means around said notched or grooved portion of said blocking means so as to hold and maintain said blocking means within said fallopian tube to provide occlusion of said fallopian tube over time;
said blocking means, flexible retaining means, and locking means designed for easy installation and removal without damaging said mesosalpinx or said fallopian tube.

2. The device according to claim 1 wherein said blocking means is a solid plug.

3. The device according to claim 1 wherein said flexible retaining means is a flexible clip.

4. The device according to claim 1 wherein said locking means is a locking barrel.

5. The device according to claim 1 wherein said blocking means, said flexible retaining means, and said locking means are each constructed of a biologically compatible material.

6. A device for effecting reversible sterilization in female mammals by means of occlusion of the fallopian tubes which comprises:
   (a) a plug for insertion into a fallopian tube, said plug comprising at least one notched or grooved portion between two end portions, said at least one notched or grooved portion being smaller in diameter than the diameter of said end portions, which end portions, in turn, are smaller in diameter than the inside diameter of said fallopian tube;
   (b) a flexible clip comprising a body portion having at least two apertures, at least one slit portion, and opening means for opening one of said at least two apertures and said slit portion for reception of the mesosalpinx and the portion of said fallopian tube which surrounds said plug; and
   (c) a locking barrel configured and dimensioned to fit into a second aperture of said flexible clip and apply force to close said first aperture of said flexible clip around said notched or grooved portion of said plug so as to hold and maintain said blocking means within said fallopian tube to provide occlusion of said fallopian tube over time;
said plug, flexible clip and locking barrel designed for easy installation and removal without damaging said mesosalpinx or said fallopian tube.

7. The device according to claim 6 wherein said plug is between about 5.0 mm and 7.0 mm in length and said end portions have an outside diameter between about 1.5 mm and 3.0 mm.

8. The device according to claim 7 wherein the notched or grooved portion of said plug is about 2.0 mm in length and between about 0.3 mm and 2.8 mm in diameter.

9. The device according to claim 8 wherein the flexible clip has an outside diameter of about 7.0 mm and a thickness of about 1.0 mm.

10. A method for effecting reversible sterilization in female mammals by occluding fallopian tubes which comprises:
    (a) inserting blocking means comprising at least one notched or grooved portion between two end portions, said at least one notched or grooved portion being smaller in diameter than the diameter of said end portions, which end portions, in turn, are smaller in diameter than the inside diameter of said fallopian tubes into each fallopian tube through its fimbriated end;
    (b) positioning flexible retaining means comprising a body portion having at least two apertures, at least one slit portion, and opening means for opening one of said at least two apertures and said slit portion for reception of the mesosalpinx and the portion of each fallopian tube which surrounds the blocking means; and
    (c) inserting locking means configured and dimensioned to fit into a second aperture of said flexible retaining means and apply force to close said first aperture of said flexible retaining means around said notched or grooved portion of said blocking means so as to hold and maintain said blocking means within each fallopian tube to provide occlusion of said fallopian tube over time.

11. A method for reversing sterilization in a female mammal sterilized according to the method of claim 10 which comprises removing said locking means, said flexible retaining means, and said blocking means from said female mammal without damaging said fallopian tube or said mesosalpinx.

12. A method for effecting reversible sterilization in female mammals by occlusion of the fallopian tubes which comprises:
    (a) inserting a plug comprising at least one notched or grooved portion between two end portions, said at least one notched or grooved portion being smaller in diameter than the diameter of said end portions, which end portions, in turn, are smaller in diameter than the inside diameter of said fallopian tubes into each fallopian tube through its fimbriated end;
    (b) positioning a flexible clip comprising a body portion having at least two apertures, at least one slit portion, and opening means for opening one of said at least two apertures and said slit portion for reception of the mesosalpinx and the portion of each fallopian tube which surrounds the plug; and
    (c) inserting a locking barrel configured and dimensioned to fit into a second aperture of said flexible clip and apply force to close said first aperture of said flexible clip around said notched or grooved portion of said plug so as to hold and maintain said plug within each fallopian tube to provide occlusion of said fallopian tubes over time.

13. A method for reversing sterilization in a female mammal sterilized according to the method of claim 12 which comprises removing said plug, said flexible clip and said locking barrel from said female mammal without damaging said fallopian tube or said mesosalpinx.

* * * * *